(12) United States Patent
Shome et al.

(10) Patent No.: US 8,880,160 B2
(45) Date of Patent: Nov. 4, 2014

(54) OPTIMIZATION OF LV AND RV LEAD PLACEMENT BASED ON ELECTRICAL DELAYS

(75) Inventors: Shibaji Shome, Arden Hills, MN (US); Pramodsingh Hirasingh Thakur, White Bear Lake, MN (US); Yinghong Yu, Shoreview, MN (US); Keith L. Herrmann, Minneapolis, MN (US); Aaron R. McCabe, Minneapolis, MN (US); Jiang Ding, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/552,996

(22) Filed: Jul. 19, 2012

(65) Prior Publication Data

US 2013/0190636 A1    Jul. 25, 2013

Related U.S. Application Data

(60) Provisional application No. 61/510,704, filed on Jul. 22, 2011, provisional application No. 61/528,013, filed on Aug. 26, 2011.

(51) Int. Cl.
| | |
|---|---|
| *A61N 1/05* | (2006.01) |
| *A61N 1/368* | (2006.01) |
| *A61N 1/39* | (2006.01) |
| *A61B 5/0456* | (2006.01) |
| *A61B 5/04* | (2006.01) |
| *A61N 1/37* | (2006.01) |
| *A61N 1/372* | (2006.01) |

(52) U.S. Cl.
CPC ............. *A61B 5/0456* (2013.01); *A61N 1/3702* (2013.01); *A61N 1/3684* (2013.01); *A61N 1/37247* (2013.01); *A61N 1/3686* (2013.01); *A61N 1/3918* (2013.01); *A61B 5/04012* (2013.01)
USPC .......................................................... 600/516

(58) Field of Classification Search
USPC .................................................. 600/516, 521
See application file for complete search history.

(56) References Cited

U.S. PATENT DOCUMENTS

| | | | |
|---|---|---|---|
| 5,527,347 | A | 6/1996 | Shelton et al. |
| 6,144,880 | A | 11/2000 | Ding et al. |

(Continued)

FOREIGN PATENT DOCUMENTS

| | | |
|---|---|---|
| WO | WO-2013009563 A1 | 1/2013 |
| WO | WO-2013016119 A1 | 1/2013 |

OTHER PUBLICATIONS

"U.S. Appl. No. 13/542,261, Advisory Action mailed Dec. 23, 2013", 3 pgs.

(Continued)

*Primary Examiner* — Paula J Stice
(74) *Attorney, Agent, or Firm* — Schwegman, Lundberg & Woessner, P.A.

(57) ABSTRACT

A system comprises a cardiac signal sensing and a processing circuit. The cardiac signal sensing circuit senses a first cardiac signal segment that includes a QRS complex and a second cardiac signal segment that includes a fiducial indicative of local ventricular activation. The processor circuit includes a site activation timer circuit configured to determine a time duration between a fiducial of the QRS complex of the first cardiac signal segment and the fiducial of the second cardiac signal segment. The processor circuit is configured to generate, using the determined time duration, an indication of optimality of placement of one or more electrodes for delivering therapy and provide the indication to at least one of a user or process.

20 Claims, 5 Drawing Sheets

(56) References Cited

U.S. PATENT DOCUMENTS

| | | |
|---|---|---|
| 6,370,427 B1 | 4/2002 | Alt et al. |
| 6,597,951 B2 | 7/2003 | Kramer et al. |
| 6,622,040 B2 | 9/2003 | Ding et al. |
| 6,671,549 B2 | 12/2003 | Van Dam et al. |
| 6,751,504 B2 | 6/2004 | Fishler |
| 6,766,189 B2 | 7/2004 | Yu et al. |
| 6,804,555 B2 | 10/2004 | Warkentin |
| 6,999,815 B2 | 2/2006 | Ding et al. |
| 7,043,301 B1 | 5/2006 | Kroll et al. |
| 7,103,412 B1 | 9/2006 | Kroll |
| 7,139,610 B2 | 11/2006 | Ferek-Petric |
| 7,181,285 B2 | 2/2007 | Lindh et al. |
| 7,209,785 B2 | 4/2007 | Kim et al. |
| 7,231,248 B2 | 6/2007 | Kramer et al. |
| 7,313,433 B2 | 12/2007 | Yu et al. |
| 7,424,324 B2 | 9/2008 | Ding et al. |
| 7,546,162 B2 | 6/2009 | Ding et al. |
| 7,558,626 B2 | 7/2009 | Corbucci |
| 7,590,446 B1 | 9/2009 | Min et al. |
| 7,630,764 B2 | 12/2009 | Ding et al. |
| 7,912,544 B1 * | 3/2011 | Min et al. .......................... 607/9 |
| 2002/0077559 A1 | 6/2002 | Ding et al. |
| 2005/0149138 A1 | 7/2005 | Min et al. |
| 2006/0241703 A1 | 10/2006 | Ding et al. |
| 2007/0208386 A1 | 9/2007 | Kramer et al. |
| 2008/0004665 A1 | 1/2008 | McCabe et al. |
| 2008/0058656 A1 | 3/2008 | Costello et al. |
| 2008/0097542 A1 | 4/2008 | Yu et al. |
| 2008/0177344 A1 | 7/2008 | Maskara et al. |
| 2008/0269822 A1 | 10/2008 | Ljungstrom et al. |
| 2009/0112276 A1 | 4/2009 | Yu et al. |
| 2009/0149904 A1 | 6/2009 | Perschbacher et al. |
| 2009/0299203 A1 | 12/2009 | De Voir et al. |
| 2009/0306732 A1 | 12/2009 | Rosenberg et al. |
| 2010/0069988 A1 | 3/2010 | Ding et al. |
| 2013/0172954 A1 | 7/2013 | Yu et al. |

OTHER PUBLICATIONS

"U.S. Appl. No. 13/542,261, Final Office Action mailed Oct. 30, 2013", 7 pgs.

"U.S. Appl. No. 13/542,261, Non Final Office Action mailed Jul. 12, 2013", 10 pgs.

"U.S. Appl. No. 13/542,261, Response filed Jun. 24, 2013 to Restriction Requirement mailed Jun. 18, 2013", 10 pgs.

"U.S. Appl. No. 13/542,261, Response filed Oct. 7, 2013 to Non Final Office Action mailed Jul. 12, 2013", 12 pgs.

"U.S. Appl. No. 13/542,261, Response filed Dec. 10, 2013 to Final Office Action mailed Oct. 30, 2013", 13 pgs.

"U.S. Appl. No. 13/542,261, Restriction Requirement mailed Jun. 18, 2013", 6 pgs.

"International Application Serial No. PCT/US2012/045543, Search Report mailed Oct. 17, 2012", 3 pgs.

"International Application Serial No. PCT/US2012/045543, Written Opinion mailed Oct. 17, 2012", 6 pgs.

"International Application Serial No. PCT/US2012/047335, Search Report mailed Oct. 17, 2012", 4 pgs.

"International Application Serial No. PCT/US2012/047335, Written Opinion mailed Oct. 17, 2012", 7 pgs.

* cited by examiner

OPTIMIZATION OF LV AND RV LEAD PLACEMENT BASED ON ELECTRICAL DELAYS

CLAIM OF PRIORITY

This application claims the benefit of priority under 35 U.S.C. §119(e) of Shome et al., U.S. Provisional Patent Application Ser. No. 61/510,704, filed on Jul. 22, 2011, and also the benefit of priority under 35 U.S.C. §119(e) of Shome et al., U.S. Provisional Patent Application Ser. No. 61/528,013, filed on Aug. 26, 2011, the benefit of priority of each of which is claimed hereby, and each of which are incorporated by reference herein in their entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices also include wearable medical devices such as wearable cardioverter defibrillators (WCDs). WCDs are monitors that include surface electrodes. The surface electrodes are arranged to provide one or both of monitoring surface electrocardiograms (ECGs) and delivering cardioverter and defibrillator shock therapy.

Some medical devices include one or more sensors to monitor different physiologic aspects of the patient. For example, the devices may derive measurements associated with a cardiac depolarization of the patient. Such monitoring devices can be implantable or wearable and the measurements can provide useful information concerning the cardiac health of the patient.

By monitoring cardiac signals indicative of expansions or contractions, IMDs can detect abnormally slow heart rate, or bradycardia. In response to an abnormally slow heart rate some CFM devices deliver electrical pacing stimulation energy to induce cardiac depolarization and contraction. The pacing stimulation energy is delivered to provide a depolarization rate that improves hemodynamic function of the patient. Delivery of pacing therapy should be optimized to ensure therapy delivery and yet avoid unnecessary stress on the heart and unnecessary reduction of battery life. Optimal selection of the site for delivery of the pacing therapy can be part of pacing therapy optimization. Optimal site selection can lead to optimized use of pacing energy and to improved hemodynamic function of the patient or subject.

OVERVIEW

This document relates generally to systems, devices, and methods that provide electrical pacing therapy to the heart of a patient or subject. In particular it relates to, systems, devices, and methods that determine a preferred site of the heart to provide pacing therapy.

A system example includes a cardiac signal sensing and a processing circuit. The cardiac signal sensing circuit senses a first cardiac signal segment that includes a QRS complex and a second cardiac signal segment that includes a fiducial indicative of local ventricular activation. The processor circuit includes a site activation timer circuit configured to determine a time duration between a fiducial of the QRS complex of the first cardiac signal segment and the fiducial of the second cardiac signal segment. The processor circuit is configured to generate, using the determined time duration, an indication of optimality of placement of one or more electrodes for delivering therapy, and provide the indication of optimality to at least one of a user or process.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device (e.g., an IMD or a wearable device) can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
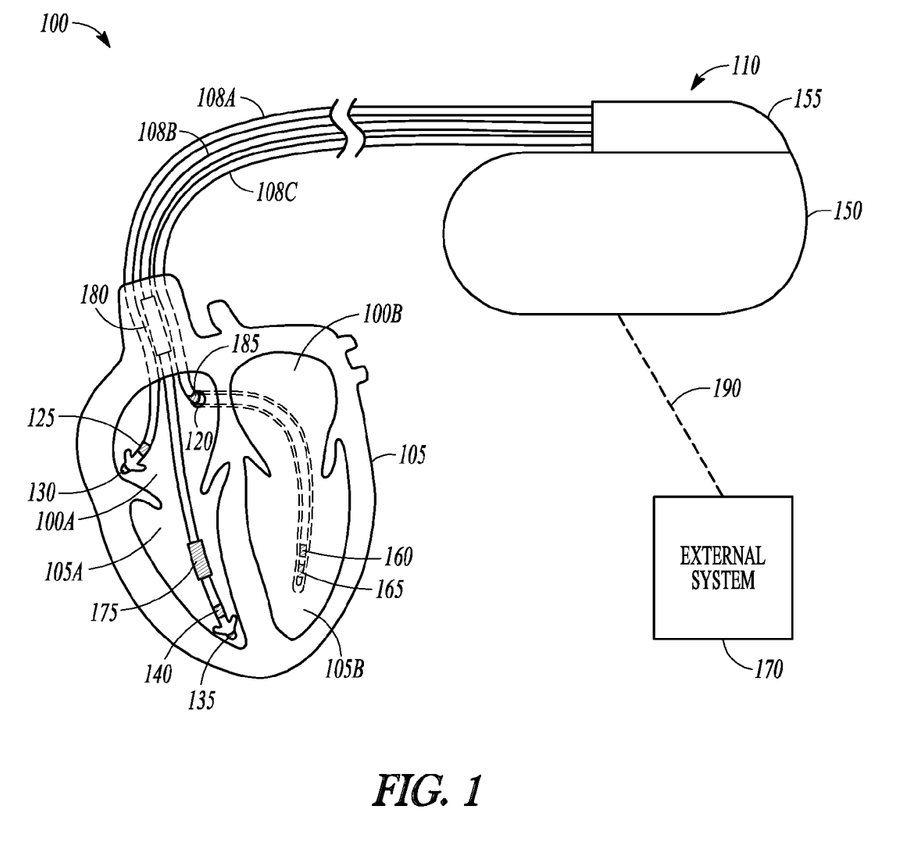
FIG. 1 is an illustration of an example of portions of a system that includes an IMD.

FIG. 1 is an illustration of an example of portions of a system 100 that uses an IMD 110 or other ambulatory medical device that can be capable of moving about with the subject, such as chronically during activities of daily living. Examples of IMD 110 include, without limitation, a pacemaker, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis or analyzed by the external device.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between the ventricles.

The IMD 110 can include a third cardiac lead 108C attached to the IMD 110 through the header 155. The third cardiac lead 108C includes electrodes 160, 162, 164, and 165 placed in a coronary vein lying epicardially on the left ventricle (LV) 105B via the coronary vein. The third cardiac lead 108C may include one or more electrodes, and may include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. The combination of electrodes used in shock therapy is sometimes called a shock channel or shock vector because the combination of electrodes can result in delivery of therapy in a particular direction. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

Figure 2:
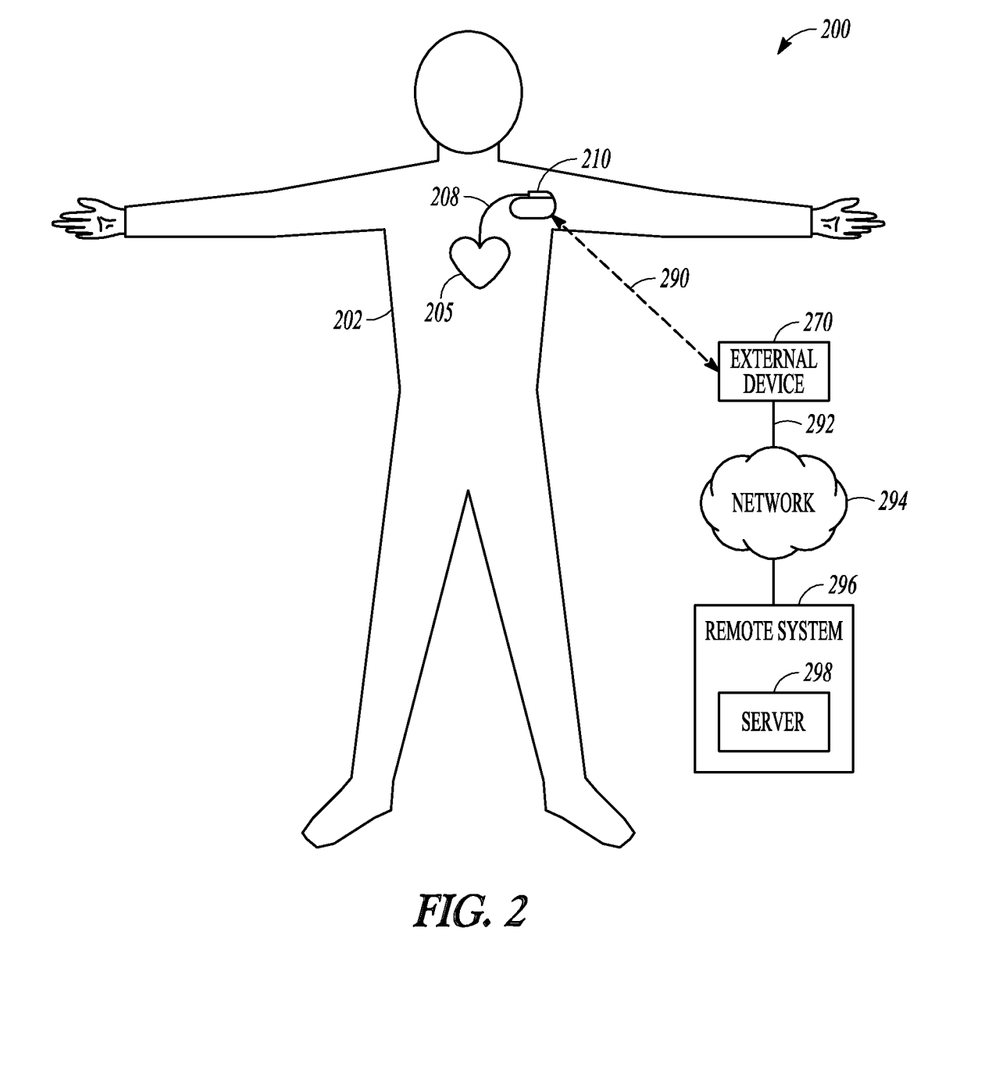
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

A medical device can monitor electrical activity of the heart of a patient. For example, a wearable device may include surface electrodes (e.g., electrodes for skin contact) to sense a cardiac signal such as an electrocardiograph (ECG) of the patient. An IMD may include implantable electrodes to sense a cardiac signal such as an internal electrogram of the patient. Measurements of the cardiac signal can provide useful information concerning the patient's cardiac health.

Providing pacing energy at an improper pacing site or location can lead to slow activation of the ventricles. Thus, it is desirable to have an IMD or other medical device that can automatically run tests to determine the best pacing site or sites, and either propose to the caregiver that these sites be used to provide the pacing therapy or automatically initiate delivery of pacing therapy to a determined optimal pacing site.

A sensed cardiac signal can include a QRS complex. The QRS complex is a waveform produced by depolarization of the ventricles and is composed of a Q-wave, an R-wave, and an S-wave. The interval from the onset of the Q-wave to the termination of the S-wave is sometimes called the QRS width or QRS duration. The time duration of the QRS complex can indicate the efficacy of the cardiac contraction.

Patients with a wide QRS complex can also be used to identify candidates to receive a CRT device. Most HF patients with wide QRS have left ventricular conduction delays (LBBB). A CRT device reestablishes electrical synchrony by pre-exciting the delayed LV area to achieve more synchronous electrical activation and thus contraction within the left ventricle. CRT may include bi-ventricular pacing or only left ventricular pacing. Methods and systems to identify whether a patient is a responder for cardiac resynchronization therapy by using width of the QRS complex can be found in Ding et al., "Identifying Heart Failure Patients Suitable for Resynchronization Therapy Using QRS complex width from an Intracardiac Electrogram," U.S. Pat. No. 7,424,324, filed May 20, 2005, which is incorporated herein by reference in its entirety.

However, the duration of the QRS complex reflects the conduction system condition of both ventricles. The Q-LV interval is the time duration from the onset of the QRS complex to the time of local LV activation at the electrode recording site. Thus, Q-LV interval reflects the time that it takes for the ventricular depolarization wavefront or activation wavefront to reach the LV electrode site. The LV-S interval is the time duration from the local depolarization activity at the LV electrode to the end of the QRS complex. Thus, LV-S interval reflects the time from the local LV depolarization activity to the time of latest activation of the left ventricle. Knowledge of one or both of the Q-LV interval and the LV-S interval can provide more information regarding optimum lead placement in the LV. Similar measurements (e.g., the Q-RV interval and the RV-S interval) can be used to guide placement of leads and electrodes in the RV.

Figure 3:
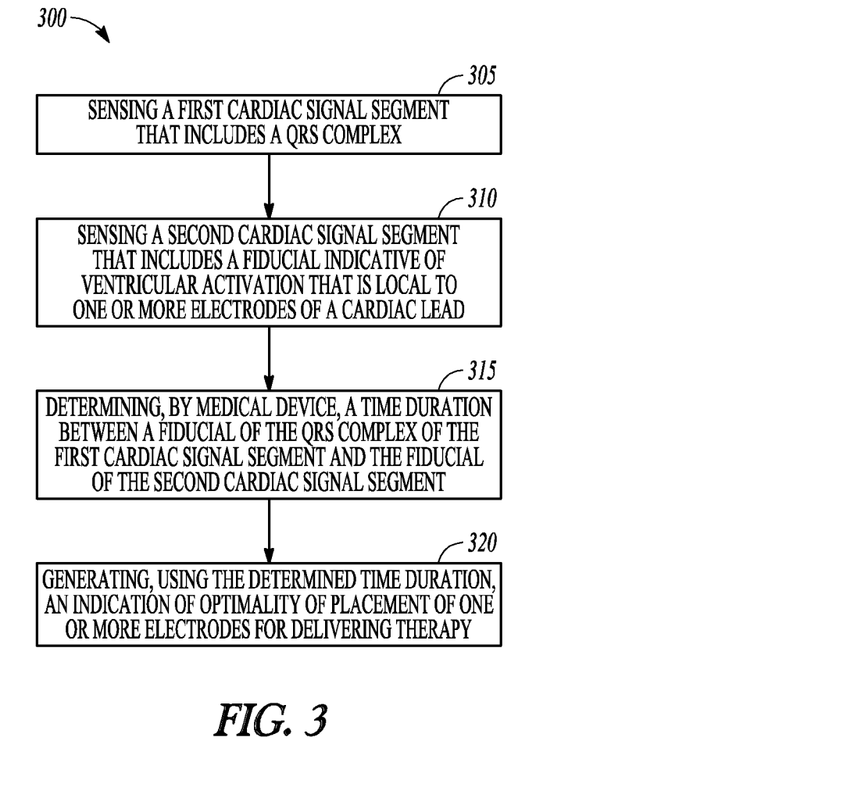
FIG. 3 shows a flow diagram of an example of a method of operating a medical device to identify an optimal site for the placement of a lead or electrodes.

FIG. 3 shows a flow diagram of an example of a method of operating a medical device to identify the optimal site or sites for the placement of electrodes for delivering pacing therapy.

At block 305, a first cardiac signal segment is sensed that includes a QRS complex. At block 310, a second cardiac signal segment is sensed. In some examples, the first and cardiac signal segments are sensed for at least one cardiac cycle. The second cardiac signal segment includes a fiducial indicative of ventricular activation that is local to one or more electrodes of a first cardiac lead. Activation refers to propagation of a depolarization wave through a chamber of the ventricles. The local activation can be LV activation or RV activation. In certain examples, activation is local when the activation occurs within ten millimeters (10 mm) of an electrode or set of electrodes.

In some examples, if the first cardiac signal segment is sensed using an implantable unipolar configuration, the second cardiac signal segment can be sensed using the same set of electrodes as the first cardiac signal segment. For example, an electrode on cardiac lead 108C in FIG. 1 and an electrode formed on the housing of the IMD. In some examples, if both the first set of electrodes and the second set of electrodes are implantable, the second set of electrodes can include at least one electrode that is different from the first set of electrodes. This provides for sensing cardiac signals using different orientations while allowing for the case where either a cathode or anode is shared between the two sets of electrodes. In some examples, the first cardiac signal segment is sensed using an external skin surface electrodes and the second cardiac signal segment is sensed using one or more electrodes of a cardiac lead.

At block 315, a time duration between a fiducial of the QRS complex of the first cardiac signal segment and the fiducial of the second cardiac signal segment is determined. Examples of a fiducial of the QRS complex include an identified R-wave and an identified Q-wave.

Figure 4:
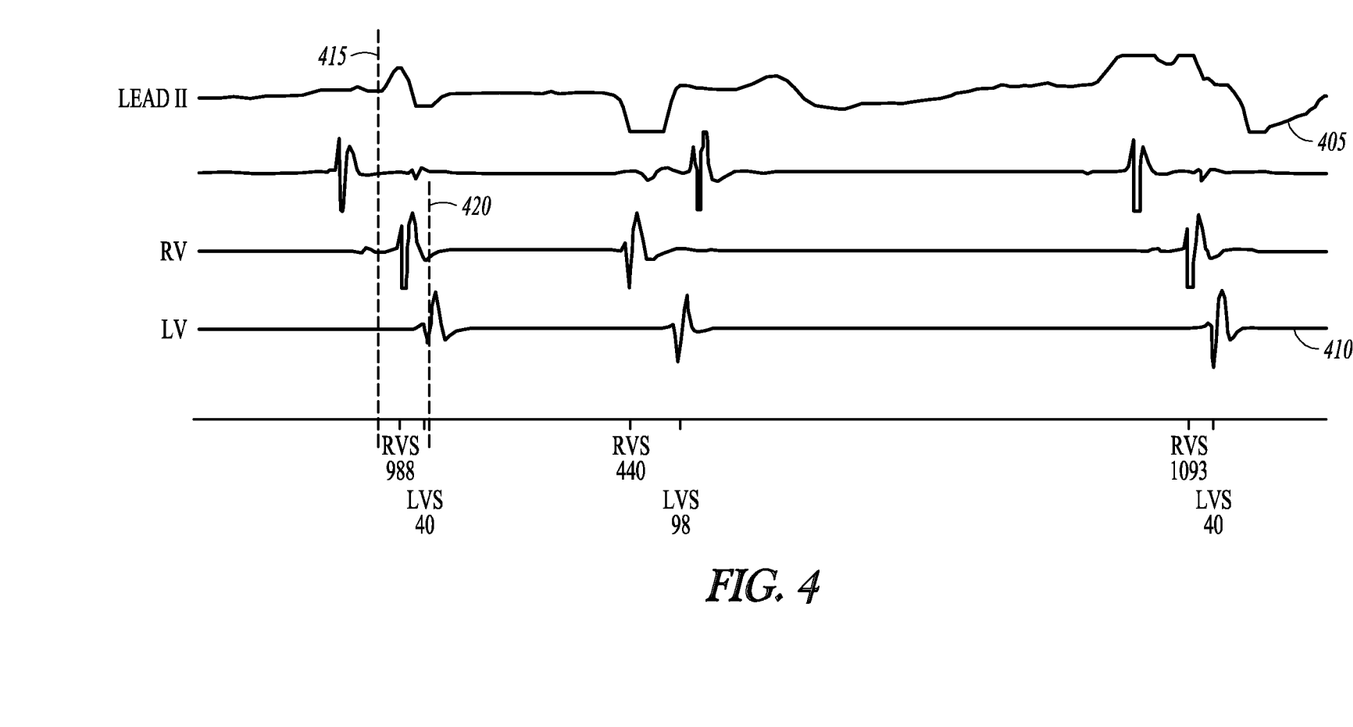
FIG. 4 shows an example of timing intervals related to ventricular depolarization.

FIG. 4 shows an example of a time duration used to determine optimum placement of electrodes or leads. The first cardiac signal segment 405 is sensed using a set of skin surface electrodes. The second cardiac signal segment 410 is an intracardiac electrogram sampled with electrodes implanted in the left ventricle of the subject. The fiducial of the QRS complex is the onset of the QRS complex 415 and the fiducial of the second cardiac signal is a time of local LV activation 420 (a Q-LV interval). The Q-LV time interval is the time measured between the vertical lines. In some examples, the two cardiac signal segments are sampled simultaneously in real time. In some examples, the two cardiac signal segments are sampled using different sampling circuits and are aligned, such as by using a timestamp associated with each cardiac signal segment.

Returning to FIG. 3, at block 320, an indication of optimality of placement of the one or more electrodes for delivering therapy is generated using the determined time duration and the indication is provided to at least one of a user or process. In the example of FIG. 4, the location corresponding to optimum placement can be the pacing site where the Q-LV interval is equal or about equal to the width of the QRS complex. In certain examples, the indication can be an identification of the best pacing site. In certain examples, the indication can be a score (e.g., a number) given to multiple candidate placements and optimality is indicated by the highest score. In certain examples, the indication can include a color (e.g., green) for the optimum location. Less than optimum sites can be indicated with a different color (e.g., yellow or red). Other indications of optimality can be used. Some examples include a numeric scale or a color scale to indicate different degrees of optimization, symbols to indicate optimization, or using words like ideal, good, fair, poor, etc.

Figure 5:
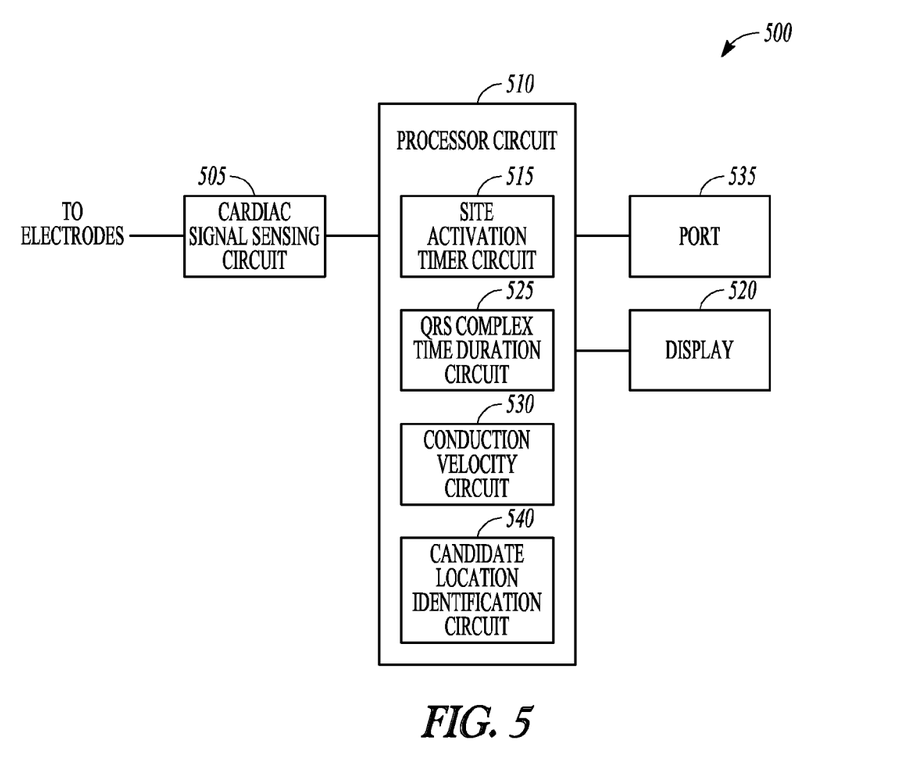
FIG. 5 is a block diagram of portions of an example of a system that identifies an optimum lead or electrode placement in a ventricle.

FIG. 5 is a block diagram of portions of an example of a system 500 that identifies an optimum lead or electrode placement in a ventricle. The system 500 includes a cardiac signal sensing circuit 505 and a processor circuit 510. The cardiac signal sensing circuit 505 can be communicatively coupled to at least a first set of electrodes and a second set of electrodes. The cardiac signal sensing circuit 505 senses a first cardiac signal segment that includes a QRS complex and senses a second cardiac signal segment. In some examples, the first cardiac signal segment is sensed using a set of electrodes that is external, such as a set of skin surface electrodes, and the second cardiac signal segment is sensed using a set of electrodes that is implantable. For instance, the system 500 may be included in a pacing system analyzer (PSA) and the cardiac signal sensing circuit 505 is connectable to the external and implantable electrodes. In certain examples, the first cardiac signal segment is sensed as an ECG and the second cardiac signal segment is sensed as an intracardiac electrogram. This is shown in the example of FIG. 4.

In some examples, both the first and second cardiac signal segments are sensed using sets of electrodes that are implantable. The system 500 may be included in a PSA connectable to the sets of implantable electrodes (e.g., electrodes incorporated into implantable leads). In some examples, the cardiac signal sensing circuit 505 is included in an implantable device (e.g., an IMD) and the processor circuit 510 is included in an external device. In certain examples, at least one electrode used to sense the second cardiac signal segment is different from the electrodes used to sense the first cardiac signal segment. In certain examples, the IMD can provide both pacing therapy and one or both of cardioversion and defibrillation therapy. The electrodes used to sense the first cardiac signal segment can be included in a shock channel of an implantable medical device or a pacing channel of the implantable medical device, and the electrodes used to sense the second cardiac signal segment can be included in a pacing channel of the implantable medical device. The first and second cardiac signal segments can both be intracardiac electrograms and the implantable device communicates electrogram information to the processor circuit (e.g., by using wireless telemetry). In certain examples, a unipolar electrode configuration is used to sense the first and second cardiac signal segments and the same electrodes are used to sense both cardiac signal segments. In certain examples, an electrode configuration is used to sense both cardiac signal segments that includes a combination of intracardiac electrodes and non-intracardiac electrodes (e.g., a patch electrode, a hemostat electrode, etc.).

The second cardiac signal segment includes a fiducial indicative of ventricular activation that is local to one or more electrodes of a first cardiac lead used to sense the cardiac signal segment. The electrode(s) of the lead may be used to sense the signal in a unipolar configuration or bipolar configuration. If the set of sensing electrodes is located in the LV, then the fiducial is indicative of local LV activation. If the set of sensing electrodes is located in the RV, then the fiducial is indicative of local RV activation.

The processor circuit 510 is communicatively coupled to the cardiac signal sensing circuit 505. The communicative coupling allows the processor circuit 510 to receive electrical signals from the cardiac signal sensing circuit 505 even though there may be intervening circuitry. As described previously, the cardiac signal sensing circuit 505 may be included in a device separate from the processor circuit 510 and the intervening circuitry may include communication circuits to communicate information wirelessly. The processor circuit 510 can be an application specific integrated circuit (ASIC), a microprocessor, a digital signal processor, or other type of processor, interpreting or executing instructions in software modules or firmware modules. The processor circuit 510 can include other circuits or sub-circuits to perform the functions described. These circuits may include software, hardware, firmware or any combination thereof. Multiple functions can be performed in one or more of the circuits as desired.

The processor circuit 510 includes a site activation timer circuit 515 that determines a time duration or time interval between a fiducial of the QRS complex of the first cardiac signal segment and the fiducial of the second cardiac signal segment. Using the determined time duration, the processor circuit 510 generates an indication of optimality of placement of one or more electrodes of the first cardiac lead for delivery of therapy (e.g., pacing therapy), and provides the indication to at least one of a user or process. In some examples, the system 500 includes a display 520 communicatively coupled to the processor circuit 510. The processor circuit 510 can present the indication of optimality to a user via the display. In some examples, the indication of optimality is provided to a separate process executing on the processor circuit 510, provided to a separate processor circuit, or provided to a process executing on a separate device.

According to some examples, the fiducial in the QRS complex of the first signal segment is the onset the QRS complex and the fiducial of the second cardiac signal segment is indicative of local LV activation. The site activation timer circuit 515 determines the time duration of the Q-LV interval. The onset of the QRS complex can be determined as a specified deviation from a determined baseline or iso-electric point for the sensed electrogram signal or ECG prior to a determined R-wave in the sensed signal. Descriptions of using a device to identify the Q-wave of a QRS complex can be found in the previously identified U.S. Pat. No. 7,424,324. The Q-LV interval is the time earliest activation of a site in the ventricle (the Q-wave onset) to the time of local LV activity (the LV time) measured using the one or more electrodes.

The Q-LV time interval can be normalized using the duration or width of the QRS complex to generate the indication of optimality of placement of one or more of the therapy electrodes. In some examples, the processor circuit includes a QRS complex time duration circuit 525 configured to measure a time duration of the QRS complex. The time duration of the QRS complex extends from the onset of the Q-wave to the termination of the S-wave, and this duration can be determined using a sensed intracardiac electrogram signal or an ECG signal. Descriptions of using devices to calculate a duration or width of a QRS complex can be found in the previously identified U.S. Pat. No. 7,424,324.

The processor circuit 510 determines a ratio that includes the measured Q-LV interval and the measured time duration of the QRS complex (e.g., (Q-LV)/($QRS_{width}$) or $QRS_{width}$/(Q-LV)) and generates the indication of optimality of placement according to a value of the determined ratio. If the processor circuit 510 generates a score as the indication, the best score would be assigned to the location of the therapy electrodes that resulted in a ratio value closest to one. This is because the placement would result in placing the therapy electrodes near the location of latest ventricular activation.

Similarly, the fiducial of the second cardiac signal segment can be indicative of local RV activation if the set of electrodes is placed in the RV. The site activation timer circuit 515 determines the time duration of the Q-RV interval, and the processor circuit 510 determines a ratio that includes the measured Q-RV time interval and the measured time duration of the QRS complex.

According to some examples, the fiducial in the QRS complex of the first cardiac signal segment is the end of the QRS complex and the fiducial of the second cardiac signal segment is indicative of local LV activation. Similar to the onset, the end of the QRS complex can be determined as a specified deviation from the baseline or from the iso-electric point for the sensed electrogram signal or ECG after the determined R-wave. Descriptions of using devices to identify the end of the QRS complex can be found in the previously identified U.S. Pat. No. 7,424,324.

The site activation timer circuit 515 measures a time interval between a fiducial in the second cardiac signal segment indicative of LV local activation and a fiducial in the first cardiac signal segment corresponding to the onset of an S-wave of the QRS complex and (LV-S interval). The processor circuit 510 is configured to generate an indication of optimality of placement according to the minimum value of the LV-S interval. The LV-S interval is representative of the time interval between local LV activation as measured at one or more electrodes of the first cardiac lead to the time of latest ventricular activation (the end QRS complex).

Minimizing this interval can indicate that the one or more electrodes are placed near the location of latest ventricular activation. In some examples, the site activation timer circuit 515 measures both the Q-LV time and LV-S time. The processor circuit 510 generates the indication of optimality of placement of the one or more electrodes using a minimization of the LV-S interval and a maximization of the Q-LV time, or using a maximization of the Q-LV time when the LV-S interval satisfies a specified threshold.

Similarly, the fiducial of the second cardiac signal segment can be indicative of RV activation if the one or more electrodes is placed in the RV. The site activation timer circuit 515 determines the time duration of the RV-S interval. The processor circuit 510 is configured to generate an indication of optimality of placement according to the minimum value of the RV-S interval. In some examples, the site activation timer circuit 515 measures both the Q-RV time and RV-S time. The processor circuit 510 generates the indication of optimality of placement for the one or more electrodes for the delivery of therapy using a minimization of the RV-S interval and a maximization of the Q-RV time.

The optimal placement site or the site of latest activation may not always be accessible for placement of the one or more electrodes. The electrodes may be incorporated into one or more implantable leads and access to the placement site can be dependent on the physiology of the heart (e.g., whether there is a vein available to access the site of latest activation). Therefore, a practical limit may have to be imposed on the S-wave time or "S time," and the adjusted S time is used in the intervals described previously. In some examples, the site activation timer circuit 515 adjusts the determined time duration according to a candidate location for the one or more electrodes for delivering therapy. The processor circuit 510 generates the indication of optimality of placement according to the adjusted determined time duration.

Local conduction velocity can be useful to determine an adjustment for the S time. In some examples, the processor circuit 510 includes a conduction velocity circuit 530 communicatively coupled to one or more electrodes of the first cardiac lead used to sense the local ventricular activation and electrodes of a second lead. The second lead is implantable and is used to sense a third cardiac signal segment. In some examples, both leads are placed in the LV. In certain examples, both sets of electrodes are both incorporated into the same LV lead. The second cardiac signal segment includes a fiducial indicative of LV activation local to the one or more electrodes of the first lead (LV1) and the third cardiac signal segment includes a fiducial indicative of LV activation that is local to one or more electrodes of the second lead (LV2). Velocity is distance divided by time. The conduction velocity circuit 530 measures a time difference ($\Delta t$) between LV 1 in the second cardiac signal segment and LV2 in the third cardiac signal segment. The distance between the electrodes of the first lead and the electrodes of the second lead will be known and can be entered into the system via a port 335 communicatively coupled to the processor circuit 510, or the distance can be pre-specified based on leads used to make the measurement. The conduction velocity circuit 530 divides the distance between the electrodes of the first lead and the second set of electrodes ($\Delta d$) by the measured time difference ($\Delta t$) to determine the local LV conduction velocity.

Similarly, the electrodes of the first lead and the electrodes of the second lead can be both placed in the RV, and the conduction velocity circuit 530 can divide the distance between the first lead electrodes and the second lead electrodes by the measured time difference to determine the RV local conduction velocity.

In some examples, the electrodes of the second lead can be placed in the RV and the one or more electrodes of the first lead can be placed in the LV. The second cardiac signal segment includes a fiducial indicative of local LV activation, and the third cardiac signal segment includes a fiducial indicative of RV activation that is local to one or more electrodes of the second lead. The conduction velocity circuit 530 can measure the time difference between the LV local activation and the RV local activation, and divide the distance between the electrodes of the first lead and the electrodes of the second lead to determine a LV local conduction velocity.

The local conduction velocity can be used to determine an offset to adjust the time duration that is used to determine the site of optimal placement of the second set of electrodes. In some examples, the system includes a port 535 that receives a distance value (e.g., via a communication port or a user interface). The distance value corresponds to a distance between the current location of the one or more electrodes of the first cardiac lead sensing the local ventricular activation and a candidate location for the one or more electrodes for delivering therapy. In certain examples, a clinician identifies the candidate location used to determine this distance. If the one or more electrodes of the first lead are placed in the LV, the conduction velocity circuit 530 determines the LV local conduction velocity. Using the LV local conduction velocity (v) and the received distance ($\Delta d$), the site activation timer circuit 515 calculates an offset time ($=\Delta d/v$). If the site activation timer circuit 515 measures the Q-LV time interval, the site activation timer circuit 515 adjusts the measured time interval by adding the calculated offset time to the measured time interval. If the one or more electrodes are placed in the RV, the conduction velocity circuit 530 measures the RV local conduction time, the site activation timer circuit 515 may measure the Q-RV interval and use the offset time to adjust the measured Q-RV interval. The adjusted Q-LV interval or Q-RV interval is used to generate the indication of optimality of placement.

According to some examples, the site activation timer circuit 515 adjusts an LV-S interval or an RV-S interval. A candidate location for delivering therapy can be received by the port 535. Also, if the electrodes of the first cardiac lead are placed in the LV, an indication of a location of a latest activation site of the LV can be received into the port. The indication can be a designation of the location or can be a distance to the location from the set of sensing electrodes. The site activation timer circuit 515 calculates an offset time using the measured LV local conduction time and the distance between the selected candidate location for the electrodes and the location of the latest LV activation site. The site activation timer circuit 515 adjusts the LV-S interval using the calculated offset time, and determines an optimum Q-LV time interval by subtracting the adjusted LV-S interval from the determined time duration of the QRS complex. The optimum Q-LV interval can be provided to a user or process.

If the one or more electrodes of the first lead are placed in the RV, an indication of a location of a latest activation site of the RV can be received into the port, the RV local conduction time is measured, the distance between the selected candidate location and the location of the latest RV activation site is determined, and an offset time is calculated using the measured RV local conduction velocity and the determined distance. If an RV-S interval is measured, the site activation timer circuit 515 adjusts the RV-S interval using the calculated offset time. The site activation timer circuit 515 determines an optimum Q-RV time interval by subtracting the adjusted RV-S interval from the determined time duration of the QRS complex.

According to some examples, the system determines one or more candidate locations for the placement of the electrodes for therapy delivery, and the locations do not need to be identified by a user. In some examples, the one or more electrodes of the first lead are placed in the LV. The site activation timer circuit 515 measures the LV-S interval, a conduction velocity circuit 530 measures the LV local conduction velocity, and a QRS complex time duration circuit measures the time duration of the QRS complex. The processor circuit 510 includes a candidate location identification circuit 540 that identifies, using the measured LV-S interval and the measured LV local conduction velocity, one or more candidate locations for electrode placement in a ventricle (e.g., in the LV). If the set of sensing electrodes is placed in the RV, the candidate location identification circuit 540 that identifies one or more candidate locations using a measured RV-S interval and a measured local RV conduction velocity.

The processor circuit 510 provides one or more indications of the one or more candidate locations to a user or process. In some examples, the candidate location identification circuit 540 calculates a distance using at least one of the LV-S interval and the LV conduction velocity ($\Delta d=\Delta t/v$), or the RV-S interval and the RV conduction velocity. Candidate locations for the one or more therapy electrodes can then be identified using the determined distance.

In some examples, the system 500 includes a display 520 communicatively coupled to the processor circuit 510. The processor circuit 510 can receive a receive image data (e.g., image data from a fluoroscope) of the location of the one or more electrodes of the first lead. The candidate location identification circuit 540 can generate a display of an image area, based on the calculated distance, overlaid on an image (e.g., a fluoroscope image) to identify one or more candidate locations for the therapy electrodes.

Figure 6:
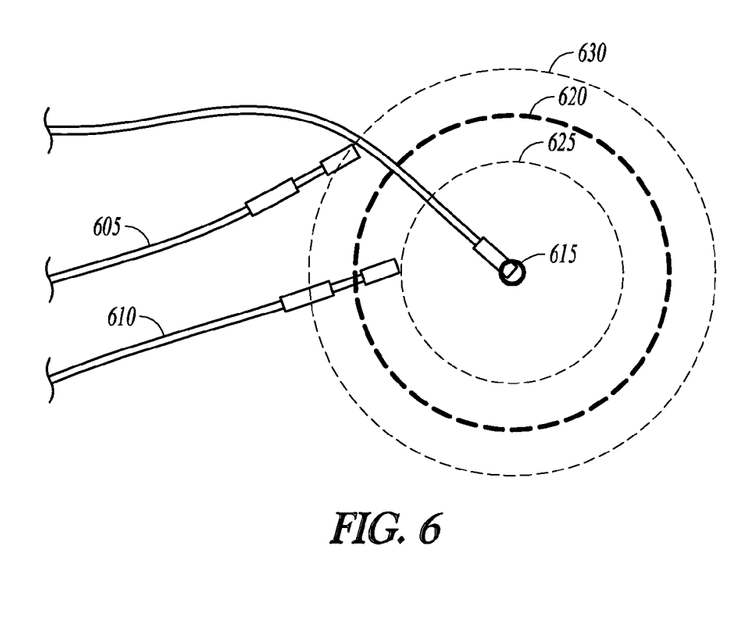
FIG. 6 shows an example of a fluoroscope image of a heart of a subject.

FIG. 6 shows an illustration of an example of a fluoroscope image of a heart of a subject. A right atrial lead 605 and a right ventricular lead 610 can be seen in the image. Also shown is an indication of a current distal electrode location 615. This corresponds to a current location of a second electrode or set of electrodes. Overlaid on the illustration of the fluoroscope image is a circle 620 having a radius equal to or about equal to a distance calculated using the local conduction velocity and the Q-LV interval. In the example shown, the Q-LV interval is 97 milliseconds (ms) and the conduction velocity is 0.25 meters per second (m/s). The QRS width was determined to be 160 ms, and the S-LV interval was 63 ms. This results in a distance of 16 mm. Thus, the radius of the circle 620 is 16 mm and the circle 620 is centered on the current location of the electrodes of the lead. The circumference of the circle represents suggested locations where electrodes can be placed to improve LV activation.

In some examples, a confidence interval can be used to further guide placement of the electrodes. The image also shows a confidence interval of +5 mm represented by a circle 625 of radius 11 mm and a circle 630 of radius 21 mm. The area between the circles represents where the electrodes should be placed. The image overlaid onto the fluoroscope image assists the physician to locate a candidate vein for placement of the lead. In some examples, the area for suggested placement of the electrodes is an arc rather than a circle. The arc extends in the basal lateral direction. In certain examples, a confidence interval is indicated about the arc.

If the subject is ischemic, the distance from the current electrode position can be weighted away from the affected area, and the candidate area for placement of the leads can be a warped circle or arc. The display of different areas of the distance from the current electrode location can be scored on the display, such as by using a color range, number or symbols to indicate optimal regions to poor regions. In some examples, the system 500 can automatically initiate programming an IMD to use an optimal pacing site based on knowledge of leads to be attached to the IMD. For instance, the system may wirelessly program an IMD to use specific electrodes of a multi-electrode LV lead.

The examples described have used an adjusted S time to determine a corrected Q-LV or Q-RV interval that is used to find an optimal placement site or sites. In some examples, a corrected QRS time is used to find the optimal placement for the one or more therapy electrodes. The corrected QRS time will be in the form QRSwidth (in ms) minus Xms, where X may be 20 ms, 30 ms, etc. The corrected QRS time is used to find the offset time. In some examples, the value of X can be found by determining the termination of the S-wave (S-point) from an intracardiac electrogram obtained from a shock channel, and determining the termination of the S-point from precordial lead. The value of X can be the time difference between the two values of the S-point multiplied by a correction factor. In some examples, the value of X can be calculated by determining the time of maximum rate of change of a unipolar LV electrogram signal (e.g., electrodes 165 and an electrode formed on the IMD header 155) just prior to the signal returning to the iso-electric point, and subtracting this determined time from an S-point measured using one or more precordial leads.

Determining the best pacing site of one or more ventricles can lead to optimal activation of the myocardial tissue. Finding the best pacing site optimizes therapy for the subject and results in best use of battery power of an IMD.

ADDITIONAL NOTES AND EXAMPLES

Example 1 includes subject matter (such as a system) comprising a cardiac signal sensing circuit and a processing circuit. The cardiac signal sensing circuit is connectable to a first cardiac lead and is configured to sense a first cardiac signal segment that includes a QRS complex and sense a second cardiac signal segment that includes a fiducial indicative of local ventricular activation at one or more electrodes of the first cardiac lead. The processor circuit is communicatively coupled to the cardiac signal sensing circuit and includes a site activation timer circuit configured to determine a time duration between a fiducial of the QRS complex of the first cardiac signal segment and the fiducial of the second cardiac signal segment. The processor circuit is configured to generate, using the determined time duration, an indication of optimality of placement of the one or more electrodes of the first cardiac lead for delivering therapy, and provide the indication to at least one of a user or process.

In Example 2, the subject matter of Example 1 can optionally include a QRS complex time duration circuit configured to measure a time duration of the QRS complex, and the site activation timer circuit can optionally be configured to measure at least one of a time interval between a fiducial of the first cardiac signal segment corresponding to an onset the QRS complex and a fiducial of the second cardiac signal segment indicative of left ventricular (LV) activation (Q-LV interval), or a time interval between the fiducial of the first cardiac signal segment corresponding to the onset of the QRS complex and a fiducial of the second cardiac signal segment indicative of right ventricular (RV) activation (Q-RV interval). The processor circuit can be configured to determine a ratio that includes the measured Q-LV interval and the measured time duration of the QRS complex, or the measured Q-RV interval and the measured time duration of the QRS complex, and generate the indication of optimality of placement according to a value of the determined ratio.

In Example 3, the subject matter of one or any combination of Examples 1 and 2 can optionally include a site activation timer circuit configured to measure at least one of a time interval between a fiducial in the second cardiac signal segment indicative of left ventricular (LV) activation and a fiducial in the first cardiac signal segment corresponding to an end of the QRS complex (LV-S interval), or a time interval between a fiducial in the second cardiac signal segment indicative of right ventricular (RV) activation and a fiducial in the first cardiac signal segment corresponding to the end of the QRS complex (RV-S interval). The processor circuit can be configured to generate an indication of optimality of placement according to at least one of a minimum LV-S interval or a minimum RV-S interval.

In Example 4, the subject matter of one or any combination of Examples 1-3 can optionally include a site activation timer circuit configured to measure at least one of a Q-LV time interval or a Q-RV time interval. The processor circuit can be configured to generate the indication of optimality of placement according to at least one of minimization of the LV-S interval and maximization of the Q-LV interval, or minimization of the RV-S interval and maximization of the Q-RV interval.

In Example 5, the subject matter of one or any combination of Examples 1-4 can optionally include a site activation timer circuit configured to adjust the determined time duration according to a candidate location for the one or more electrodes for delivering therapy, and the processor circuit can be configured to generate the indication of optimality according to the adjusted determined time duration.

In Example 6, the subject matter of one or any combination of Examples 1-5 can optionally include a port communicatively coupled to the processor circuit and configured to receive a distance value, wherein the distance value corresponds to a distance between the current location of the one or more electrodes of the first cardiac lead and a candidate location for the one or more electrodes for delivering therapy. The processor circuit can include a conduction velocity circuit configured to measure at least one of an LV conduction velocity local to the current location of the one or more electrodes, or an RV conduction velocity local to the current location. The site activation timer circuit can optionally be configured to measure at least one of a Q-LV time interval or a Q-RV time interval, calculate an offset time using the at least one of the measured LV local conduction velocity and the received distance, or the measured RV local conduction velocity and the received distance; and adjust the measured at least one of the Q-LV time interval or the Q-RV interval by adding the calculated offset time to the measured time interval. The processor circuit can be configured to generate the indication of optimality of placement according to the adjusted at least one of the Q-LV interval or the Q-RV interval.

In Example 7, the subject matter of one or any combination of Examples 1-6 can optionally include a site activation timer circuit configured to measure at least one of an LV-S interval or an RV-S interval. The processor circuit can optionally include a QRS complex time duration circuit configured to measure a time duration of the QRS complex, a conduction velocity circuit configured to measure at least one of an LV conduction velocity local to the current location of the one or more electrodes of the first cardiac lead, or an RV conduction velocity local to the current location, and a candidate location identification circuit. The candidate location identification circuit is configured to identify, using the measured LV-S interval and the measured local LV conduction velocity, or using the measured RV-S interval and the measured local RV conduction velocity, one or more candidate locations for electrode placement in a ventricle for delivering therapy, and provide one or more indications of the one or more candidate locations to a user or process.

In Example 8, the subject matter of one or any combination of Examples 1-7 can optionally include a port communicatively coupled to the processor circuit and configured to receive a selection of the candidate location for electrode placement for delivery of therapy and receive at least one of an indication of a location of a latest activation site of the LV or an indication of a location of a latest activation site of the RV. The processor circuit optionally includes a conduction velocity circuit configured to measure at least one of an LV conduction velocity local to the current location of the one or more electrodes of the first cardiac lead, or an RV conduction velocity local to the current location. The site activation timer circuit can optionally be configured to measure at least one of an LV-S interval or an RV-S interval calculate an offset time using the measured the LV local conduction velocity or the RV local conduction velocity and a distance between the selected candidate location and the location of the latest LV or RV activation site, adjust the at least one of the measured LV-S interval or RV-S interval using the calculated offset, determine at least one of an optimum Q-LV time interval by subtracting the adjusted LV-S interval from the determined time duration of the QRS complex, or an optimum Q-RV time interval by subtracting the adjusted RV-S interval from the determined time duration of the QRS complex, and provide the at least one of the determined optimum Q-LV interval or Q-RV interval to a user or process.

In Example 9, the subject matter of one or any combination of Examples 1-8 can optionally include a display communicatively coupled to the processor circuit. The site activation timer circuit can optionally be configured to measure at least one of an LV-S interval or an RV-S interval according to the current location of the one or more electrodes of the first cardiac lead. The processor circuit optionally includes a conduction velocity circuit configured to measure at least one of an LV local conduction velocity or an RV local conduction velocity according to the current location, a port to receive a fluoroscope image of the current location, and a candidate location identification circuit. The candidate location identification circuit can be configured to calculate a distance using at least one of the LV-S interval and the LV conduction velocity, or the RV-S interval and the RV conduction velocity, and generate a display of an image area, based on the calculated distance, overlaid on the fluoroscope image to identify candidate locations for electrode placement.

In Example 10, the subject matter of one or any combination of Examples 1-9 can optionally include a cardiac signal sensing circuit is connectable to a set of skin surface electrodes and configured to sense the first cardiac signal segment using the set of skin surface electrodes sense the second cardiac signal segment using the one or more electrodes of the first cardiac lead.

In Example 11, the subject matter of one or any combination of Examples 1-10 can optionally include one or more electrodes of the first cardiac lead that are implantable and included in a pacing channel of an implantable medical device. The first cardiac signal segment can be sensed using a set of implantable electrodes included in at least one of a shock channel or pacing channel of the implantable medical device.

Example 12 can include subject matter, or can optionally be combined with the subject matter of one or any combination of Examples 1-11 to include subject matter (such as a method, a means for performing acts, or a machine-readable medium including instructions that, when performed by the machine, cause the machine to perform acts) comprising sensing a first cardiac signal segment that includes a QRS complex, sensing a second cardiac signal segment that includes a fiducial indicative of local ventricular activation at one or more electrodes of a first cardiac lead, determining, by the medical device, a time duration between a fiducial of the QRS complex of the first cardiac signal segment and the fiducial of the second cardiac signal segment, generating, using the determined time duration, an indication of optimality of placement of the one or more electrodes of the first cardiac lead for delivering therapy, and providing the indication to at least one of a user or process.

In Example 13, the subject matter of Example 12 can optionally include measuring a time duration of the QRS complex, and measuring at least one of a time interval between a fiducial of the first cardiac signal segment corresponding to an onset of the QRS complex and a fiducial of the second cardiac signal segment indicative of left ventricular (LV) activation (Q-LV interval), or a time interval between the fiducial of the first cardiac signal segment corresponding to the onset of the QRS complex and a fiducial of the second cardiac signal segment indicative of right ventricular (RV) activation (Q-RV interval). The subject matter can further include determining a ratio that includes at least one of the measured Q-LV interval and the measured time duration of the QRS complex, or the measured Q-RV interval and the measured time duration of the QRS complex, and generating the indication according to a value of the determined ratio.

In Example 14, the subject matter of one or any combination of Examples 12 and 13 can optionally include measuring at least one of a time interval between a fiducial in the second cardiac signal segment indicative of left ventricular (LV) activation and a fiducial in the first cardiac signal segment corresponding to an end of the QRS complex and (LV-S interval), or a time interval between a fiducial in the second cardiac signal segment indicative of right ventricular (RV) activation and a fiducial in the first cardiac signal segment corresponding to the end of the QRS complex and (RV-S interval), and generating the indication according to at least one of a minimum LV-S interval or a minimum RV-S interval.

In Example 15, the subject matter of one or any combination of Examples 12-14 can optionally include measuring at least one of a Q-LV time interval and the LV-S interval, or a Q-RV time interval and the RV-S interval, and generating the indication according to at least one of minimization of the LV-S interval and maximization of the Q-LV interval, or minimization of the RV-S interval and maximization of the Q-RV interval.

In Example 16, the subject matter of one or any combination of Examples 12-15 can optionally include adjusting the determined time duration according to a candidate location for the one or more electrodes for delivering therapy, and generating the indication according to the adjusted determined time duration.

In Example 17, the subject matter of one or any combination of Examples 12-16 can optionally include determining at least one of a Q-LV interval or a Q-RV interval, measuring an LV local conduction velocity or an RV local conduction velocity according to a current location of the set of sensing electrodes, receiving a distance value into the medical device, wherein the distance value corresponds to a distance between the current location of the one or more electrodes of the first cardiac lead and the candidate location, calculating an offset time using at least one of the LV local conduction velocity and the received distance, or the RV local conduction velocity and the received distance, adjusting the at least one of the Q-LV interval or Q-RV interval by adding the calculated offset time to the determined time duration, and generating the indication according to the adjusted at least one of the Q-LV interval or the Q-RV interval.

In Example 18, the subject matter of one or any combination of Examples 12-17 can optionally include measuring at least one of an LV-S interval or an RV-S interval, measuring an LV local conduction velocity or an RV local conduction velocity according to the current location of the set of sensing electrodes, identifying one or more candidate locations for electrode placement in a ventricle for delivering therapy, and providing one or more indications of the one or more candidate locations to a user or process.

In Example 19, the subject matter of one or any combination of Examples 12-18 can optionally include receiving a selection of the candidate location for the one or more electrodes into the medical device, receiving, according to the candidate location, a location of a latest activation site of the LV or a location of a latest activation site of the RV into the medical device, measuring, according to the current location of the one or more electrodes of the first cardiac lead, an LV local conduction velocity or an RV local conduction velocity, calculating an offset time using the measured the LV local conduction velocity or the RV local conduction velocity and a distance between the selected candidate location and the location of the latest LV or RV activation site, adjusting at least one of the LV-S interval or the RV-S interval using the calculated offset, measuring a time duration of the QRS complex, determining at least one of an optimum Q-LV time interval by subtracting the adjusted LV-S interval from the determined time duration of the QRS complex or an optimum Q-RV time interval by subtracting the adjusted RV-S interval from the determined time duration of the QRS complex, and providing the at least one of the determined optimum Q-LV interval or Q-RV interval to a user or process.

In Example 20, the subject matter of one or any combination of Examples 12-19 can optionally include measuring at least one of an LV-S interval and an LV conduction velocity local to the current location of the one or more electrodes of the first cardiac lead, or an RV-S interval and an RV conduction velocity local to the current location of the one or more electrodes, receiving a fluoroscope image of the current location of the one or more electrodes, calculating a distance using at least one of the LV-S interval and the LV conduction velocity, or the RV-S interval and the RV conduction velocity, and identifying candidate locations for placement of the one or more electrodes for delivering therapy by generating a display of an image area, based on the calculated distance, overlaid on the fluoroscope image.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." In the event of inconsistent usages between this document and documents incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
    a cardiac signal sensing circuit connectable to a first cardiac lead configured for use in a ventricle, the cardiac signal sensing circuit configured to:
        sense a first cardiac signal segment that includes a QRS complex; and
        sense a second cardiac signal segment that includes a local activation fiducial indicative of a cardiac depolarization wavefront arriving at or near one or more electrodes of the first cardiac lead; and
    a processor circuit communicatively coupled to the cardiac signal sensing circuit, wherein the processor circuit includes a site activation timer circuit configured to determine a time duration between a fiducial of the QRS complex of the first cardiac signal segment and the local activation fiducial of the second cardiac signal segment, and wherein the processor circuit is configured to:
        generate, using the determined time duration, an indication of optimality of placement of the one or more electrodes of the first cardiac lead for delivering therapy; and
        provide the indication to a cas one of a user or process.

2. The system of claim 1,
    wherein the processor circuit includes a QRS complex time duration circuit configured to measure a time duration of the QRS complex,
    wherein the site activation timer circuit is configured to measure at least one of:
        a time interval between a fiducial of the first cardiac signal segment corresponding to an onset the QRS complex and a fiducial of the second cardiac signal segment indicative of left ventricular (LV) activation (Q-LV interval), or
        a time interval between the fiducial of the first cardiac signal segment corresponding to the onset of the QRS complex and a fiducial of the second cardiac signal segment indicative of right ventricular (RV) activation (Q-RV interval), and wherein the processor circuit is configured to:
    determine a ratio that includes the measured Q-LV interval and the measured time duration of the QRS complex, or the measured Q-RV interval and the measured time duration of the QRS complex, and
    generate the indication of optimality of placement according to a value of the determined ratio.

3. The system of claim 1,.
    wherein the site activation timer circuit is configured to measure at least one of:
        a time interval between a fiducial in the second cardiac signal segment indicative of left ventricular (LV) activation and a fiducial in the first cardiac signal segment corresponding to an end of the ORS complex (LV-S interval), or
        a time interval between a fiducial in the second cardiac signal segment indicative of right ventricular (RV) activation and a fiducial in the first cardiac signal segment corresponding to the end of the QRS complex (RV-S interval), and
    wherein the processor circuit is configured to generate an indication of optimality of placement according to at least one of a minimum LV-S interval or a minimum RV-S interval.

4. The system of claim 3,
    wherein the site activation timer circuit is configured to measure at least one of a Q-LV time interval or a Q-RV time interval, and
    wherein the processor circuit is configured to generate the indication of optimality of placement according to at least one of minimization of the LV-S interval and maximization of the Q-LV interval, or minimization of the RV-S interval and maximization of the Q-RV interval.

5. The system of claim 1,
    wherein the site activation timer circuit is configured to adjust the determined time duration according to a candidate location for the one or more electrodes for delivering therapy, and
    wherein the processor circuit is configured to generate the indication of optimality according to the adjusted determined time duration.

6. The system of claim 5, including
    a port communicatively coupled to the processor circuit and configured to receive a distance value, wherein the distance value corresponds to a distance between the current location of the one or more electrodes of the first cardiac lead and a candidate location for the one or more electrodes for delivering therapy,
    wherein the processor circuit includes a conduction velocity circuit configured to measure at least one of an LV conduction velocity local to the current location of the one or more electrodes, or an RV conduction velocity local to the current location, and
    wherein the site activation timer circuit is configured to:
        measure at least one of a Q-LV time interval or a Q-RV time interval;
        calculate an offset time using the at least one of the measured LV local conduction velocity and the received distance, or the measured RV local conduction velocity and the received distance; and adjust the measured at least one of the Q-LV time interval or the Q-RV interval by adding the calculated offset time to the measured time interval, and wherein the processor circuit is configured to generate the indication of optimality of placement according to the adjusted at least one of the Q-LV interval or the Q-RV interval.

7. The system of claim 5, wherein the site activation timer circuit is configured to measure at least one of an LV-S interval or an RV-S interval, wherein the processor circuit includes:

a QRS complex time duration circuit configured to measure a time duration of the QRS complex;

a conduction velocity circuit configured to measure at least one of an LV conduction velocity local to the current location of the one or more electrodes of the first cardiac lead, or an RV conduction velocity local to the current location; and a candidate location identification circuit configured to:
identify, using the measured LV-S interval and the measured local LV conduction velocity, or using the measured RV-S interval and the measured local RV conduction velocity, one or more candidate locations for electrode placement in a ventricle for delivering therapy, and provide one or more indications of the one or more candidate locations to a user or process.

8. The system of claim 5, including a port communicatively coupled to the processor circuit and configured to:

receive a selection of the candidate location for electrode placement for delivery of therapy; and receive at least one of an indication of a location of a latest activation site of the LV or an indication of a location of a latest activation site of RV, wherein the processor circuit includes a conduction velocity circuit configured to measure at least one of an LV conduction velocity local to the current location of the one or more electrodes of the first cardiac lead, or an RV conduction velocity local to the current location, and wherein the site activation timer circuit is configured to:
measure at least one of an LV-S interval or an RV-S interval;

calculate an offset time using the measured the LV local conduction velocity or the RV local conduction velocity and a distance between the selected candidate location and the location of the latest LV or RV activation site;

adjust the at least one of the measured LV-S interval or RV-S interval using the calculated offset;

determine at least one of an optimum Q-LV time interval by subtracting the adjusted LV-S interval from the determined time duration of the QRS complex, or an optimum Q-RV time interval by subtracting the adjusted RV-S interval from the determined time duration of the QRS complex; and provide the at least one of the determined optimum Q-LV interval or Q-RV interval to a user or process.

9. The system of claim 5, including:

a display communicatively coupled to the processor circuit;

wherein the site activation timer circuit is configured to measure at least one of an LV-S interval or an RV-S interval according to the current location of the one or more electrodes of the first cardiac lead, and wherein the processor circuit includes:

a conduction velocity circuit configured to measure at least one of an LV local conduction velocity or an RV local conduction velocity according to the current location;

a port to receive a fluoroscope image of the current location; and a candidate location identification circuit configured to:
calculate a distance using at least one of the LV-S interval and the LV conduction velocity, or the RV-S interval and the RV conduction velocity; and generate a display of an image area, based on the calculated distance, overlaid on the fluoroscope image to identify candidate locations for electrode placement.

10. The system of claim 1, wherein the cardiac signal sensing circuit is connectable to a set of skin surface electrodes and configured to sense the first cardiac signal segment using the set of skin surface electrodes sense the second cardiac signal segment using die one or more electrodes of the first cardiac lead.

11. The system of claim 1, wherein the one or more electrodes of the first cardiac lead are implantable and included in a pacing channel of an implantable medical device, and wherein the first cardiac signal segment is sensed using a set of implantable electrodes included in at least one of a shock channel or pacing channel of the implantable medical device.

12. A method of operating a medical device, the method comprising:

sensing a first cardiac signal segment that includes a QRS complex;

sensing a second cardiac signal segment that includes a local activation fiducial indicative of a cardiac depolarization wavefront arriving at or near one or more electrodes of a first cardiac lead;

determining, by the medical device, a time duration between a fiducial of the QRS complex of the first cardiac signal segment and the local activation fiducial of the second cardiac signal segment;

generating, using the determined time duration, an indication of optimality of placement of the one or more electrodes of the first cardiac lead for delivering therapy; and providing the indication to at least one of a user or process.

13. The method of claim 12, including:

measuring a time duration of the QRS complex;

wherein determining the time duration between the fiducial of the QRS complex and the fiducial of the second cardiac signal segment includes measuring at least one of:

a time interval between a fiducial of the first cardiac signal segment corresponding to an onset of the QRS complex and a fiducial of the second cardiac signal segment indicative of left ventricular (LV) activation (Q-LV interval), or a time interval between the fiducial of the first cardiac signal segment corresponding to the onset of the QRS complex and a fiducial of the second cardiac signal segment indicative of right ventricular (RV) activation (Q-RV interval), wherein the method further includes determining a ratio that includes at least one of the measured Q-LV interval and the measured time duration of the QRS complex, or the measured Q-RV interval and the measured time duration of the QRS complex, and wherein generating the indication of optimality of placement includes generating the indication according to a value of the determined ratio.

14. The method of claim 12,
wherein determining the time duration between the fiducial of the QRS complex in the first cardiac signal segment and the fiducial of the second cardiac signal segment includes measuring at least one of:
- a time interval between a fiducial in the second cardiac signal segment indicative of left ventricular (LV) activation and a fiducial in the first cardiac signal segment corresponding to an end of the QRS complex and (LV-S interval), or
- a time interval between a fiducial in the second cardiac signal segment indicative of right ventricular (RV) activation and a fiducial in the first cardiac signal segment corresponding to the end of the QRS complex and (RV-S interval), and wherein generating the indication of optimality of placement includes generating the indication according to at least one of a minimum LV-S interval or a minimum RV-S interval.

15. The method of claim 14, including:
measuring at least one of a Q-LV time interval and the LV-S interval, or a Q-RV time interval and the RV-S interval, and
wherein generating the indication of optimality of placement of the one or more electrodes includes generating the indication according to at least one of minimization of the LV-S interval and maximization of the Q-IN interval, or minimization of the RV-S interval and maximization of the Q-RV interval.

16. The method of claim 12, including:
adjusting the determined time duration according to a candidate location for the one or more electrodes for delivering therapy, and
wherein generating the indication of optimality of placement includes generating the indication according to the adjusted determined time duration.

17. The method of claim 16,
wherein the determined time duration includes at least one of a Q-LV interval or a Q-RV interval;
wherein adjusting the determined time duration includes:
  measuring an LV local conduction velocity or an RV local conduction velocity according to a current location of the set of sensing electrodes;
  receiving a distance value into the medical device, wherein the distance value corresponds to a distance between the current location of the one or more electrodes of the first cardiac lead and the candidate location;
  calculating an offset time using at least one of the LV local conduction velocity and the received distance, or the RV local conduction velocity and the received distance; and
  adjusting the at least one of the Q-LV interval or Q-RV interval by adding the calculated offset time to the determined time duration, and
wherein generating the indication of optimality of placement includes generating the indication according to the adjusted at least one of the Q-LV interval or the Q-RV interval.

18. The method of claim 16,
wherein determining the time duration between the fiducial of the QRS complex in the first cardiac signal segment and the fiducial of the second cardiac signal segment includes measuring at least one of an LV-S interval or an RV-S interval, and wherein the method further includes:
  measuring an LV local conduction velocity or an RV local conduction velocity according to the current location of the set of sensing electrodes;
  identifying one or more candidate locations for electrode placement in a ventricle for delivering therapy; and
  providing one or more indications of the one or more candidate locations to a user or process.

19. The method of claim 16,
wherein adjusting the determined time duration includes:
  receiving a selection of the candidate location for the one or more electrodes into the medical device;
  receiving, according to the candidate location, a location of a latest activation site of the LV or a location of a latest activation site of the RV into the medical device;
  measuring, according to the current location of the one or more electrodes of the first cardiac lead, an LV local conduction velocity or an RV local conduction velocity;
  calculating an offset time using the measured the LV local conduction velocity or the RV local conduction velocity and a distance between the selected candidate location and the location of the latest LV or RV activation site; and
  adjusting at least one of the LV-S interval or the RV-S interval using the calculated offset; and
wherein the method further includes:
  measuring a time duration of the QRS complex;
  determining at least one of an optimum Q-LV time interval by subtracting the adjusted LV-S interval from the determined time duration of the QRS complex or an optimum Q-RV time interval by subtracting the adjusted RV-S interval from the determined time duration of the QRS complex; and
  providing the at least one of the determined optimum Q-LV interval or Q-RV interval to a user or process.

20. The method of claim 16, including:
measuring at least one of an LV-S interval and an LV conduction velocity local to the current location of the one or more electrodes of the first cardiac lead, or an RV-S interval and an RV conduction velocity local to the current location of the one or more electrodes;
receiving a fluoroscope image of the current location of the one or more electrodes;
calculating a distance using at least one of the LV-S interval and the LV conduction velocity, or the RV-S interval and the RV conduction velocity; and
identifying candidate locations for placement of the one or more electrodes for delivering therapy by generating a display of an image area, based on the calculated distance, overlaid on the fluoroscope image.

* * * * *